United States Patent [19]

Shah

[11] Patent Number: 5,434,158

[45] Date of Patent: Jul. 18, 1995

[54] SPIRO-SUBSTITUTED AZACYCLES AS NEUROKININ-3 ANTAGONISTS

[75] Inventor: Shrenik K. Shah, Metuchen, N.J.

[73] Assignee: Merck & Co., Inc., Rahway, N.J.

[21] Appl. No.: 233,487

[22] Filed: Apr. 26, 1994

[51] Int. Cl.$^6$ .................. A61K 31/44; A61K 31/495; C07D 221/00; C07D 401/00

[52] U.S. Cl. ..................... 514/278; 514/252; 514/255; 514/329; 514/331; 544/360; 544/400; 546/16; 546/17; 546/223; 546/233

[58] Field of Search ................. 546/16, 17; 514/278

[56] References Cited

U.S. PATENT DOCUMENTS 4,420,485 12/1983 Davis et al. .................... 546/17
5,091,387 2/1992 Evans et al. .................... 546/17

FOREIGN PATENT DOCUMENTS

0428434A2 5/1991 European Pat. Off.
0431943A2 6/1991 European Pat. Off.
0474561A1 3/1992 European Pat. Off.

OTHER PUBLICATIONS

Biochem and Biophys Res. Comm vol. 184, No. 3, pp. 1418–1424 (May 15, 1992).
Life Sciences, vol. 50, No. 15, pp. PL-101 PL-106 (1992).
J. Pharmacol (1993) 108, 844–851, Y. Hirayama, et al.
J. Auton Pharmacol (1993) 13, 23–93, C. Alberto Maggi, et al.
Biochem. and Biophys. Res. Comm. vol. 198, No. 3, 1994 pp. 961–966.
Biochem. and Biophys. Res. Comm. vol. 198, No. 3, 1994 pp. 967–972.
C. A. Maggai, et al., Regulatory Peptides 53 (1994) pp. 259–274 "Tachykinin NK3 receptor mediates NANC hyperpolarization and relaxation via nitric oxide in the circular muscle . . . ".

Primary Examiner—Cecilia Tsang
Attorney, Agent, or Firm—Curtis C. Panzer; David L. Rose

[57] ABSTRACT

Disclosed are spiro-substituted azacycles of formula I

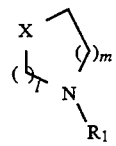

are selective neurokinin-3 antagonists useful in the treatment of CNS disorders.

4 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO (iv) ANIT-SENSE: NO (xi) SEQUENCE DESCRIPTION: SEQ ID NO:1:

Met Leu Gly Phe Phe Gln Gln Pro Lys Pro Arg
1               5                   10

(2) INFORMATION FOR SEQ ID NO:2:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:2:

Met Leu Gly Val Phe Ser Asp Thr Lys His
1               5                   10

(2) INFORMATION FOR SEQ ID NO:3:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:3:

Gly Pro Tyr Trp Gly His Ser Trp His Xaa
1               5                   10

SPIRO-SUBSTITUTED AZACYCLES AS NEUROKININ-3 ANTAGONISTS

BACKGROUND OF THE INVENTION

The invention disclosed herein is directed to certain spiro-substituted azacycles useful as tachykinin receptor antagonists. In particular, the compounds disclosed herein are neurokinin-3 receptor antagonists.

The tachykinins, substance P (SP), neurokinin A (NKA) and neurokinin B (NKB), are structurally similar members of a family of neuropeptides. Each of these is an agonist of the receptor types, neurokinin-1 receptor (NK-1), neuorokinin-2 receptor (NK-2) and neuorokinin-3 receptor (NK-3), which are so defined according to their unique amino acid sequence and their relative abilities to bind tachykinins with high affinity and to be activated by the natural agonists SP, NKA and NKB respectively.

The tachykinins are distinguished by a conserved carboxyl-terminal sequence Phe-X-Gly-Leu-Met-NH$_2$. More specifically, substance P is a pharmacologically-active neuropeptide that is produced in mammals and possesses a characteristic amino acid sequence:

SEQ ID NO:1: Arg-Pro-Lys-Pro-Gln-Gln-Phe-Phe-Gly-Leu-Met-NH$_2$

Neurokinin A possesses the following amino acid sequence:

SEQ ID NO:2: His-Lys-Thr-Asp-Ser-Phe-Val-Gly-Leu-Met-NH$_2$.

Neurokmin B possesses the following amino acid sequence:

SEQ ID NO:3: Asp-Met-His-Asp-Phe-Phe-Val-Gly-Leu-Met-NH$_2$.

(Chang et al., Nature New Biol. 232, 86 (1971); D. F. Veber et al., U.S. Pat. No. 4,680,283).

The neurokinin receptors are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, Pharmacol. Rev., 1983, 35, 85–141). The NK1 and NK2 receptor subtypes are implicated in synaptic transmission (Laneuville et al., Life Sci., 42:1295–1305 (1988)).

Substance P acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al., Science, 199, 1359 (1978); P. Oehme et al., Science, 208, 305 (1980)) and plays a role in sensory transmission and pain perception (T. M. Jessell, Advan. Biochem. Psychopharmacol. 28, 189 (1981)). In particular, substance P has been shown to be involved in the transmission of pain in migraine (see B. E. B. Sandberg et al., Journal of Medicinal Chemistry, 25, 1009 (1982)), and in arthritis (Levine et al. Science, (1984) 226 547–549).

In the airways, it has been indicated that NK1 receptors are associated with microvascular leakage and mucus secretion, while NK2 receptors regulate smooth muscle contraction. Also, it has been shown that both substance P and neurokinin A are effective in inducing airway constriction and edema. Based on such findings, it is believed that substance P and neurokinin A may be involved in the pathogenesis of neurogenic inflammation, including allergic diseases such as asthma. (Frossard et al., Life Sci., 49, 1941–1953 (1991); Advenier, et al., Biochem. Biophys. Res. Comm., 184(3), 1418–1424 (1992)).

In experimental studies, sensory neuropeptides, especially tachykinins such as substance P and neurokinin A, can bring about many of the pathophysiological features of asthma. Neurokinin A is a very potent constrictor of human airways in vitro, and substance P causes mucus secretion in the airways. (Barnes P. J., Lancet, pp242–44 (1986); Rogers D. R., Aursudkij B., Barnes P. J., Euro. J. Pharmacol, 174, 283–86 (1989)).

Inhalation of bradykinin causes bronchoconstriction in asthmatic patients but not in normal subjects. (Fuller R. W., Dixon C. M. S., Cuss F. M. C., Barnes P. J., Am Rev Respir Dis, 135, 176–80 (1987)). Since the bradykinin-induced bronchoconstriction is partly opposed by anticholinergic agents and since bradykinin is only a weak constrictor of human airways in vitro, it has been suggested that the bronchoconstrictor response is partly mediated by a neural reflex. Bradykinin stimulates vagal afferent C fibers and causes bronchoconstriction in dogs. (Kaufman M. P., Coleridge H. M., Coleridge J. C. G., Baker D. G., J. Appl. Physio., 48, 511–17 (1980)). In guinea-pig airways, bradykinin causes a bronchoconstrictor response by way of cholinergic and sensory-nerve-mediated mechanisms. (Ichinoe M., Belvisi M. G., Barnes P. J., J. Pharmacol. Exp. Ther., 253, 594–99 (1990). Bradykinin-induced bronchoconstriction in human airways may therefore be due partly to tachykinin released from sensory nerve terminals via axon reflex mechanisms. Clinical trials have shown that a dual NK-1/NK-2 antagonist (such as FK-224) protects against bradykinin induced bronchocontriction in asthmatic patients. (Ichinoe, M. et al., Lancet,, vol. 340, pp 1248–1251 (1992)).

The tachykinins have also been implicated in gastrointestinal (GI) disorders and diseases of the GI tract, such as inflammatory bowel disease, ulcerative colitis and Crohn's disease, etc. (see Mantyh et al., Neuroscience, 25 (3), 817–37 (1988) and D. Regoli in "Trends in Cluster Headache" Ed. F. Sicuteri et al., Elsevier Scientific Publishers, Amsterdam, 1987, pp. 85–95).

It is also hypothesized that there is a neurogenic mechanism for arthritis in which substance P may play a role (Kidd et al., "A Neurogenic Mechanism for Symmetric Arthritis" in The Lancet, 11 November 1989 and Gronblad et al., "Neuropeptides in Synovium of Patients with Rheumatoid Arthritis and Osteoarthritis" in J. Rheumatol. (1988) 15(12) 1807–10). Therefore, substance P is believed to be involved in the inflammatory response in diseases such as rheumatoid arthritis and osteoarthritis (O'Byrne et al., in Arthritis and Rheumatism (1990) 33 1023–8). Other disease areas where tachykinin antagonists are believed to be useful are allergic conditions (Hamelet et al., Can. J. Pharmacol. Physiol. (1988) 66 1361–7), immunoregulation (Lotz et al., Science (1988) 241 1218–21, Kimball et al., J. Immunol. (1988) 141 (10) 3564–9 and A. Perianin, et al., Biochem. Biophys. Res. Commun. 161,520 (1989)) vasodilation, bronchospasm, reflex or neuronal control of the viscera (Mantyh et al., PNAS (1988) 85 3235–9) and, possibly by arresting or slowing $\beta$-amyloid-mediated neurodegenerative changes (Yankner et al., Science, (1990) 250, 279–82) in senile dementia of the Alzheimer type, Alzheimer's disease and Downs Syndrome. Substance P may also play a role in demyelinating diseases such as multiple sclerosis and amyotrophic lateral sclerosis [J. Luber-Narod et. al., poster presented at C.I.N.P. XVIIIth Congress, 28th June–2nd July, 1992]. Antagonists selective for the substance P and/or the neurokinin A receptor may be useful in the treatment of asthmatic disease (Frossard et al., Life Sci., 49, 1941–1953 (1991); Advenier, et al., Biochem. Biophys. Res. Comm., 184(3), 1418–1424 (1992)). These antagonists may also be useful in the treatment of emesis. See C. Bountra, K. Bounce, T. Dale, C. Gardner, C. Jordan. D. Twissell and P. Ward, Eur. J. Pharmacol., 249. R3–R4 (1993) "Anti-emetic profile of a non-peptide neurokinin NK1 receptor antagonist, CP-99,994, in the ferret.

The localisation of tachykinins and neurokinin receptor subtypes within the striatum is also heterogeneous. NKB immunoreactive fibres are colocalised within GABA containing neurones that project to the palladium but not the substantia nigra pars reticulata, whereas the SP containing neurones project principally to the substantia nigra pars reticulata. See Burgunder, J. M., & Young, W. S. 1989. Distribution, projection, and dopaminergic regulation of the neurokinin B mRNA-containing neurones of the rat caudate-putamen. Neurosci. 32, 323–335. Activation of tachykinin receptors in the straitum modulates the release of neurotransmitters including acetylcholine and dopamine See Tremblay, L., Kemel, M-L. Desban, M., Gauchy, C., & Glowinski, J. 1992. Distinct presynaptic control of dopamine release in stirosomal-matrix-enriched areas of the rat striatum by selective agonists of NK1, NK2 and NK3 tachykinin receptors. Proc. Natl. Acad. Sci. U.S.A. 89, 11214–11218. Interestingly in that study the release of dopamine by [Pro$^7$]NKB (NK3) in the matrix compartment was insensitive to tetrodotoxin suggesting a presynaptic localisation of NK$_3$ receptors.

This hypothesis is further supported by the finding that the NKB-induced stimulation of acetylchlorine release in rat striatum is reduced by both TTX and by lesions of the nigrostriatal pathway, and is consistent with the presence of NK$_3$ receptors on dopamine cell bodies of the striatonigral and mesolimbic pathways. See Arenas, E., Alberch, J., Perez-Navarro, E., Solsona, C., Marsal, J. 1991. Neurokinin receptors differentially mediate endogenous acetylcholine release evoked by tachykinins in the neostriatum. J. Neurosci. 11 (8), 2332–2338; and Keegan, K. D., Woodruff, G., & Pinnock, R. D. 1992. The selective NK3 receptor agonist senktide excites a subpopulation of dopamine-sensitive neurones inthe rat substantia nigra pars compact in vitro. Br. J. Pharmacol. 105, 3–5.

We have found that Tachykinin receptor subtype on presumed dopamine neurones of the rat ventral tegmental area are a NK3 and not a NK1 or NK2 receptor subtype. These data suggest that NK3 receptors mediate the principal excitatory influence of tachykinins on mesolimbic dopamine neurones; however the role of receptors on afferent projections to the VTA and the relative tone of neuropeptide-containing fibres may have a more significant influence over their function.

Binding studies have shown NK$_3$-receptors to be present in brain slices from several species eg rat, mouse and guinea-pig, however, Dietl & Palacios, using $^{125}$I- labelled Bolton Hunter (BH) eledoisin reported an absence of NK3-receptors in primate and human brain. The human NK3-receptor was cloned from human brain mRNA, indicating that the protein is expressed in this tissue. See Huang, et al, BBRC 184:996–972 (1992). However, the cloned human NK3-receptor has lower affinity for eledoisin thatn the rat receptor and this probably explains the apparent absence of NK3-binding sites in human brain when 125I-BHeledoisin is used as the ligand. Indeed, using 3H-senktide Guard & Watson readily demonstrated the presence of NK3-binding sites in primate brain. See Dietl, M. M. & Palacios, J. M. Phylogeny and tachykinin receptor localisation in the vertebrate central nervous system: apparent absence of neurokinin-2 and neurokinin-3 binding sites in the human brain. 1991 Br Res 539:211–222; Buell, G., Schultz, S. J., Arkinstal, S. J., Maury, K., Missotten, M., Adami, N., Talabot, F. & Kawashin, E. Molecular characterisation, expression and localisation of human neurokinin-3 receptor. 1992 Febs Letts 299, 90–95; and Guard, S. & Watson, S. P. 1991 Neurochem Int 18:149–165.

Interestingly, infusion of senktide (an NK3-receptor agonist) by microdialysis in the substantia nigra and VTA of the rat caused behavioural responses characteristic of the activation of dopaminergic pathways and this effect was different with age. This observation implies that neurokinin receptors may play a role in central dopaminergic disorders, particularly those such as Parkinsonism which are more prelevant in advanced age. See Stoessl, A. J., Polanski, E. & Frydryszak, H. Effects of ageing on tachykinin function in the basal ganglia. 1993 Brain Res 632: 21–28.

SUMMARY OF THE INVENTION

This invention is directed to compounds of formula I.

The invention is also concerned with pharmaceutical formulations with these novel compounds as active ingredients and the use of the novel compounds and their formulations in the treatment of certain disorders including CNS disorders.

The compounds of this invention are tachykinin receptor antagonists, in particular, neurokinin-3 receptor antagonists, and are useful in the treatment of inflammatory diseases, pain, migraine, asthma, emesis and CNS disorders.

DETAILED DESCRIPTION OF THE INVENTION

This invention is directed to compounds of formula I.

or a pharmaceutically acceptable salt thereof, wherein the nitrogen expressly shown above is optionally quaternized with $C_{1-4}$alkyl or phenyl $C_{1-4}$alkyl or is optionally present as the N-oxide ($N^+O^-$), and wherein:

l and m are each independently 0, 1, 2, 3, 4, or 5, with the proviso that l+m is equal to 1, 2, 3, 4, or 5;

$R_1$ is

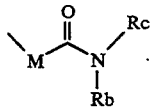

M is selected from a group consisting of:
  linear or branched $C_{1-8}$ alkyl, linear or branched $C_{2-8}$ alkenyl, wherein the $C_{1-8}$ alkyl or $C_{2-8}$ alkenyl is optionally mono or di- substituted, the substitutents independently selected from:
(a) hydroxy,
(b) cyano,
(c) halogen which is defined to include Br, Cl, I, and F,
(d) trifluoromethyl,
(e) phenyl or mono, di or trisubstituted phenyl, the substitutents independently selected from
  (1) phenyl,
  (2) $C_{1-3}$alkyl,
  (3) $C_{1-3}$alkoxy,
  (4) cyano,
  (5) halogen,
  (6) trifluoromethyl,
(7) —$NR_6COR_7$, wherein $R_6$ and $R_7$ are independently selected from:
  (a) hydrogen,
  (b) $C_{1-6}$ alkyl, or mono or disubstituted $C_{1-6}$ alkyl, the substitutents independently selected from
    (1) phenyl,
    (2) hydroxy,
    (3) oxo,
    (4) cyano,
    (5) $C_{1-3}$alkoxy,
    (6) trifluoromethyl,
  (c) phenyl or mono, di or trisubstituted phenyl, the substitutents independently selected from
    (1) hydroxy,
    (2) $C_{1-3}$alkyl,
    (3) cyano,
    (4) halogen,
    (5) trifluoromethyl,
  or
  $R_6$ and $R_7$ are joined together to form a 5-, 6-, or 7-membered monocyclic saturated ring containing 1 or 2 heteroatoms independently selected from nitrogen, oxygen, and sulfur, and in which the ring is unsubstituted or mono or disubstituted, the substituents independently selected from
    (a) hydroxy,
    (b) oxo,
    (c) cyano,
    (d) halogen,
    (e) trifluoromethyl,
(8) —$NR_6CO_2R_7$,
(9) —$NR_6CONHR_7$,
(10) —$NR_6S(O)_jR_7$, wherein j is 1 or 2,
(11) —$CONR_6R_7$,
(12) —$COR_6$,
(13) —$CO_2R_6$,
(14) —$OR_6$,
(15) —$S(O)_{k'}R_6$ wherein k' is 0, 1 or 2, (f) heteroaryl, wherein heteroaryl is selected from the group consisting of:
  (1) benzimidazolyl,
  (2) benzofuranyl,
  (3) benzoxazolyl,
  (4) furanyl,
  (5) imidazolyl,
  (6) indolyl,
  (7) isooxazolyl,
  (8) isothiazolyl,
  (9) oxadiazolyl,
  (10) oxazolyl,
  (11) pyrazinyl,
  (12) pyrazolyl,
  (13) pyridyl,
  (14) pyrimidyl,
  (15) pyrrolyl,
  (16) quinolyl,
  (17) tetrazolyl,
  (18) thiadiazolyl,
  (19) thiazolyl,
  (20) thienyl,
  (21) triazolyl, wherein the heteroaryl is unsubstituted or mono di or trisubstituted, the substituents independently selected from
  (1) phenyl,
  (2) hydroxy,
  (3) cyano,
  (4) halogen,
  (5) trifluoromethyl, Rb is selected from the group consisting of
  (a) $C_{1-3}$alkyl,
  (b) hydroxy$C_{1-3}$alkyl,
  (c) hydrogen, and
  (d) trifluoromethyl, Rc is substituted branched or linear $C_{1-4}$alkyl wherein the substituent is selected from the group consisting of
  (a) $C_{1-3}$alkyl,
  (b) hydroxy$C_{1-3}$alkyl
  (c) $C_{1-3}$alkoxy,
  (d) halogen,
  (e) trifluoromethyl;
  (f) hydrogen,
  (g) phenyl or mono, di or trisubstituted phenyl, the substitutents independently selected from
    (1) hydroxy,
    (2) cyano,
    (3) halogen,
    (4) trifluoromethyl,
    (5) $C_{1-3}$alkyl,
    (6) $C_{1-3}$alkoxy, X is

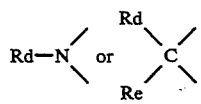

Rd is selected from a group consisting of:
  (1) hydrogen,
  (2) $C_{1-8}$ linear or branched alkyl, unsubstituted, monosubstituted or multiply substituted with
    (a) —OH, (b) —OR$_6$,
(c) =O,
(d) —NHCOR$_6$,
(e) —NR$_6$R$_7$,
(f) —CN,
(g) —halogen,
(h) —CF$_3$,
(i) —phenyl, unsubstituted or substituted, wherein the substitutents are selected from the group consisting of
  (1) hydroxy,
  (2) cyano,
  (3) halogen,
  (4) trifluoromethyl,
(3) phenyl or mono, di or trisubstituted phenyl, the substituents independently selected from
  (1) hydroxy,
  (2) cyano,
  (3) —C(O)NR$_6$R$_7$,
  (4) —NR$_6$R$_7$,
  (5) —NR$_6$COR$_7$,
  (6) —halogen,
  (7) —CF$_3$, and
  (8) C$_{1-3}$ alkyl,
(4) aryl or mono, di or trisubstituted aryl wherein the aryl is selected from the group consisting of
  (a) benzimidazolyl,
  (b) benzofuranyl,
  (c) benzoxazolyl,
  (d) furanyl,
  (e) imidazolyl,
  (f) indolyl,
  (g) isoxazolyl,
  (h) isothiazolyl,
  (i) oxadiazolyl,
  (j) oxazolyl,
  (k) pyrazinyl,
  (l) pyrazolyl,
  (m) pyridyl,
  (n) pyrimidyl,
  (o) pyrrolyl,
  (p) quinolyl,
  (q) tetrazolyl,
  (r) thiadiazolyl,
  (s) thiazolyl,
  (t) thienyl, and
  (u) triazolyl,
wherein the substituents are each independently selected from
  (1) hydroxy,
  (2) cyano,
  (3) —C(O)NR$_6$R$_7$,
  (4) —NR$_6$R$_7$,
  (5) —NR$_6$COR$_7$,
  (6) —halogen,
  (7) —CF$_3$, and
  (8) C$_{1-3}$ alkyl,
Re is selected from the group consisting of
(1) C$_{1-6}$ alkyl, branched or unbranched, unsubstituted or mono or disubstituted, the substituents being selected from hydrogen and hydroxy,
(2) hydroxy,
(3) OR$_6$, wherein R$_6$ is as defined immediately above,
(4) halogen,
(5) trifluoromethyl,
(6) nitro,
(7) cyano,
(8) NR$_6$R$_7$,
(9) NHCOR$_6$,
(10) NR$_6$COR$_7$,
(11) NHCO$_2$R$_6$,
(12) NR$_6$CO$_2$R$_7$,
(13) NHS(O)$_j$R$_6$,
(14) NR$_6$S(O)$_j$R$_7$,
(15) CONR$_6$R$_7$,
(16) COR$_6$,
(17) CO$_2$R$_6$, and
(18) S(O)$_j$R$_6$;
or Rd and Re are joined together to form a mono- or disubstituted saturated or unsaturated monocyclic or bicyclic ring of 5, 6, 7, 8, 9, or 10 atoms including the carbon to which Rd and Re are attached, wherein 0, 1, or 2 of said atoms may be heteroatoms independently selected from N, O, or S,
wherein the substituents are each independently selected from
  (1) hydroxy,
  (2) oxo,
  (3) cyano,
  (4) —C(O)NR$_6$R$_7$,
  (5) —NR$_6$R$_7$,
  (6) —NR$_6$COR$_7$,
  (7) —halogen,
  (8) —CF$_3$,
  (9) —C$_{1-3}$ alkyl,
  (10) —S(O)2 C$_{1-3}$alkyl, and
  (11) —C(O)R$_6$.
One genus within this embodiment is the compounds of formula I wherein:
l+m is equal to 2, or 3;
R$_1$ is $$\underset{\underset{Rb}{\big|}}{M}-\overset{O}{\overset{\|}{C}}-\underset{}{N}-Rc$$

M is selected from a group consisting of:
C$_2$, C$_3$ or C$_4$ linear or branched alkyl, unsubstituted or mono, di or tri substituted, the substitutents independently selected from:
(a) hydroxy,
(b) Cl or F,
(c) phenyl or mono, di or trisubstituted phenyl, the substitutents independently selected from
  (1) hydroxy,
  (2) C$_{1-3}$alkyl,
  (3) halogen,
  (4) —NR$_6$COR$_7$, wherein R$_6$ and R$_7$ are independently selected from:
    (a) hydrogen,
    (b) C$_{1-4}$alkyl, or mono or disubstituted C$_{1-4}$alkyl, the substituents independently selected from
      (1) phenyl,
      (2) hydroxy,
      (3) oxo,
      (4) halogen, or
    (c) phenyl or mono di or trisubstituted phenyl, the substitutents independently selected from
      (1) hydroxy,
      (2) C$_{1-3}$alkyl,
      (3) cyano,
      (4) halogen,
      (5) trifluoromethyl,
or $R_6$ and $R_7$ are joined together to form a 5-, 6-, or 7-membered monocyclic saturated ting containing 1 or 2 heteroatoms independently selected from nitrogen, oxygen, and sulfur, and in which the ring is unsubstituted or mono or disubstituted, the substituents independently selected from
  (a) hydroxy,
  (b) oxo,
  (c) cyano,
  (d) halogen,
  (5) —$NR_6CO_2R_7$,
  (6) —$NR_6CONHR_7$,
  (7) —$NR_6S(O)_jR_7$, wherein j is 1 or 2,
  (8) —$CONR_6R_7$,
  (9) —$COR_6$,
  (10) —$CO_2R_6$,
  (11) —$OR_6$,
  (12) —$S(O)_{k'}R_6$, wherein k' is 0, 1, or 2,
  (d) heteroaryl, wherein heteroaryl is selected from the group consisting of:
    (1) pyrazinyl,
    (2) pyrazolyl,
    (3) pyridyl,
    (4) pyrimidyl,
    (5) thienyl, and
    (6) indolyl,
  wherein the heteroaryl is unsubstituted or mono di or trisubstituted, the substituents independently selected from
    (a) phenyl,
    (b) hydroxy, and
    (c) halogen,
Rb is selected from the group consisting of
  (a) $C_{1-3}$alkyl, and
  (b) hydrogen,
Rc is substituted branched or linear $C_{1-4}$alkyl wherein the substituent is selected from the group consisting of
  (a) $C_{1-3}$alkyl,
  (b) $C_{1-3}$alkoxy,
  (c) hydrogen,
  (d) phenyl or mono or di- isubstituted phenyl, the substitutents independently selected from
    (1) halogen,
    (2) trifluoromethyl,
    (3) $C_{1-3}$alkyl,
X is $$Rd-N\diagdown^{Rd}\diagup \quad \text{or} \quad \diagdown C\diagup^{\diagdown}_{Re}$$

Rd is selected from a group consisting of:
  (1) $C_{1-8}$ linear or branched alkyl, unsubstituted, monosubstituted or multiply substituted with
    (a) —OH,
    (b) —$OR_6$,
    (c) =O,
    (d) —$NHCOR_6$,
    (e) —$NR_6R_7$,
    (f) —phenyl, unsubstituted or substituted, wherein the substitutents are selected from the group consisting of
      (1) hydroxy,
      (2) cyano,
      (3) halogen,
      (4) trifluoromethyl,
    (2) phenyl or mono or di- substituted phenyl, the substituents independently selected from
      (1) hydroxy,
      (2) cyano,
      (3) —$C(O)NR_6R_7$,
      (4) —$NR_6R_7$,
      (5) —$NR_6COR_7$,
      (6) —halogen,
      (7) —$CF_3$, and
      (8) $C_{1-3}$ alkyl,
    (3) aryl or mono, di or trisubstimted aryl wherein the aryl is selected from the group consisting of
      (a) benzimidazolyl,
      (b) benzofuranyl,
      (c) benzoxazolyl,
      (d) furanyl,
      (e) imidazolyl,
      (f) indolyl,
      (g) isooxazolyl,
      (h) isothiazolyl,
      (i) oxadiazolyl,
      (j) oxazolyl,
      (k) pyrazinyl,
      (l) pyrazolyl,
      (m) pyridyl,
      (n) pyrimidyl,
      (o) pyrrolyl,
      (p) quinolyl,
      (q) tetrazolyl,
      (r) thiadiazolyl,
      (s) thiazolyl,
      (t) thienyl, and
      (u) triazolyl,
    wherein the substituents are independently selected from
      (1) hydroxy,
      (2) cyano,
      (3) —$NR_6R_7$,
      (4) —$NR_6COR_7$,
      (5) —halogen,
      (6) —$CF_3$, and
      (7) $C_{1-3}$ alkyl,
Re is selected from the group consisting of
  (1) $C_{1-6}$ alkyl, branched or unbranched, unsubstituted or mono or disubstituted, the substituents being selected from hydrogen and hydroxy,
  (2) hydroxy,
  (3) $OR_6$, wherein $R_6$ is as defined immediately above,
  (4) halogen,
  (5) trifluoromethyl,
  (6) nitro,
  (7) cyano,
  (8) $NR_6R_7$,
  (9) $NHCOR_6$,
  (10) $NR_6COR_7$,
  (11) $NHCO_2R_6$,
  (12) $NR_6CO_2R_7$,
  (13) $NHS(O)_jR_6$,
  (14) $NR_6S(O)_jR_7$,
  (15) $CONR_6R_7$,
  (16) $COR_6$,
  (17) $CO_2R_6$, and
  (18) $S(O)_jR_6$;
or R d and Re are joined together to form a mono- or di- substituted saturated or unsaturated monocyclic or bicyclic ring of 5, 6, 7, 8, 9, or 10 atoms including the carbon to which Rd and Re are attached, whrerin 0, 1, or 2 of said atoms may be heteroatoms independently selected from N, O, or S, wherein the substituents independently selected from
(1) oxo,
(2) —C(O)NR$_6$R$_7$,
(3) —NR$_6$R$_7$,
(4) —NR$_6$COR$_7$,
(5) —halogen,
(6) —C$_{1-3}$ alkyl,
(7) —S(O)$_2$ C$_{1-3}$alkyl, and
(8) —C(O)R$_6$.

One class within this genus are the compounds of formula I wherein:

M is selected from a group consisting of:
C$_2$, C$_3$, or C$_4$ mono or di- substituted, the substitutent independently selected from:
(a) hydroxy,
(b) Cl or F,
(c) phenyl or mono or di-substituted phenyl, the substitutents independently selected from
(1) C$_{1-3}$alkoxy,
(2) C$_{1-3}$alkyl,
(3) halogen, Rb is selected from the group consisting of
(a) C$_{1-3}$alkyl, and
(b) hydrogen, Rc is phenylC$_{1-4}$alkyl wherein the phenyl is optionally mono, di- or trisubstituted, the substitutents independently selected from
(1) halogen,
(2) trifluoromethyl,
(3) C$_{1-3}$alkyl.

One subclass within this class are the compounds of formula I wherein:

R$_1$ is

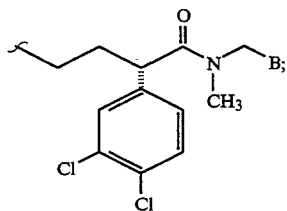

where B is
(a) phenyl or mono, di or tri- substituted phenyl wherein the substitutents are independently chloro, methyl, phenyl or CF$_3$;
(b) pyridyl or mono di or trisubstituted pyridyl wherein the substitutents are independently chloro, methyl, phenyl or CF$_3$; and
(c) thiophene or mono or disubstituted thiophene wherein the substitutents are independently chloro, methyl, phenyl or CF$_3$.

A second genus within the above described embodiment are the compounds of formula I wherein;

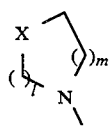

is optionally mono di or trisubstituted, wherein the group is selected from

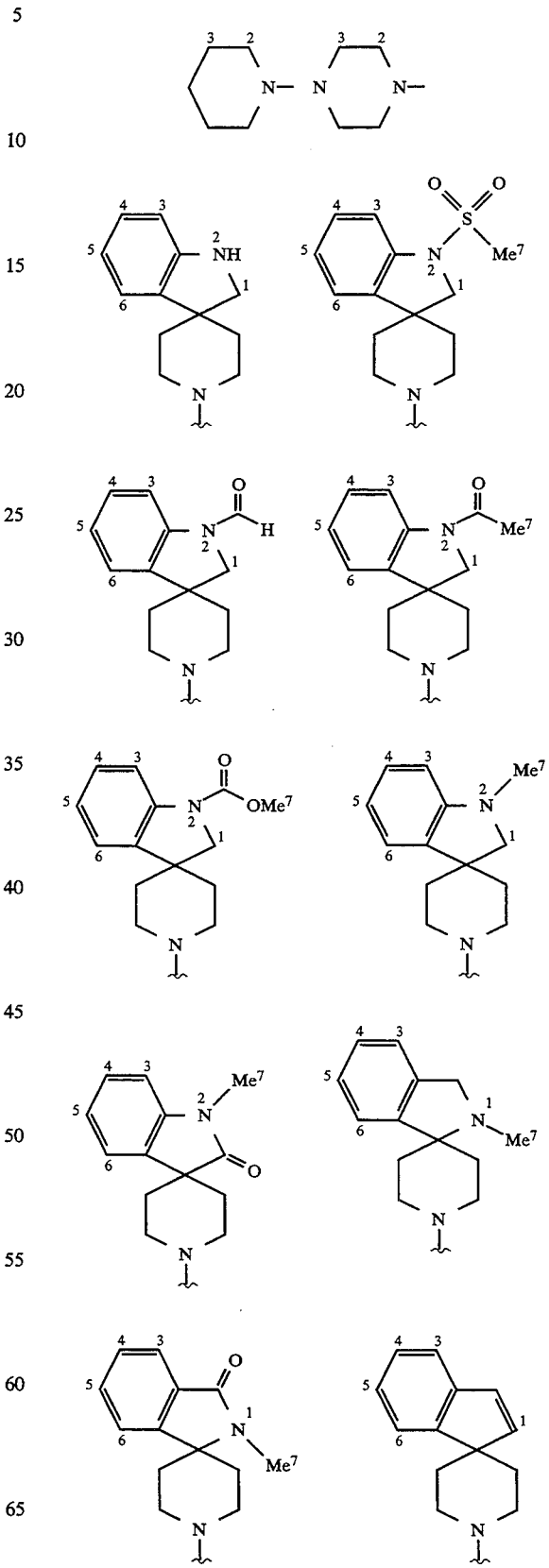

-continued

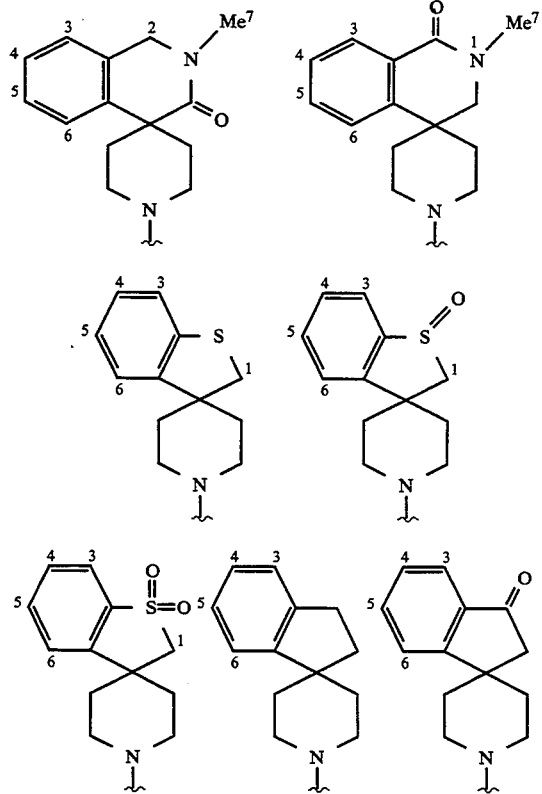

the optional substitutents residing at 1, 2, or 3 of the positions 1, 2, 3, 4, 5, 6, 7 and 8 of the above groups, the substituents selected from the group consisting of
(1) hydroxy,
(2) cyano,
(3) —C(O)NR$_6$R$_7$,
(4) —NR$_6$R$_7$,
(5) —NR$_6$COR$_7$,
(6) —halogen,
(7) —CF$_3$,
(8) —C$_{1-3}$ alkyl,
(9) —S(O)$_2$ C$_{1-3}$alkyl.

As is clear from the examples and schemes, the designation:

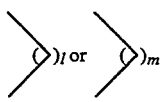

in formula I is interchangable with (CH$_2$)$_l$ or (CH$_2$)$_m$ respectively. As appreciated by those of skill in the art, halo as used herein are intended to include chloro, fluoro, bromo and iodo.

Exemplifying the invention are the compounds of the examples including the group consisting of
(a) 1′[3-(S)-(3,4-dichlorophenyl)-4-(N-benzyl-N-methyl)amino-4-oxo-butyl]-1-methanesulfonyl-spiro[indoline-3,4′-piperidine];
(b) 1′[3-(S)-(3,4-dichlorophenyl)-4-(N-benzyl-N-methyl)amino-4-oxo-butyl]-spiro[1H-indene-1,4′-piperidine];
(c) 1′[3-(S)-(3,4-dichlorophenyl)-4-(N-benzyl-N-methyl)amino-4-oxo-butyl]]-spiro[(3-indanone)-1,4′-piperidine];
(d) 1-[3-(S)-(3,4-dichlorophenyl)-4-(N-benzyl-N-methyl)amino-4-oxo-butyl]-4-phenyl-4-acetamido-piperidine;
(e) 1-[3-(S)-(3,4-dichlorophenyl)-4-(N-benzyl-N-methyl)amino-4-oxo-butyl]-4-benzyl-piperazine;
(f) 1-[3-(S)-(3,4-dichlorophenyl)-4-(N-benzyl-N-methyl-)amino-4-oxo-butyl]-4-phenyl-piperidine].
(g) 1-[3-(S)-(3,4-dichlorophenyl)-4-(N-benzyl-N-methyl)amino-4-oxo-butyl]-4-(2-pyridyl)-piperazine; and
(h) 1′[3-(S)-(3,4-dichlorophenyl)-4-(N-benzyl-N-methyl)amino-4-oxo-butyl]-1-acetyl-spiro[indoline-3,4′-piperidine].

Compounds of formula I within the scope of this invention are further detailed in the claims appended to this application.

In an alternative embodiment may be co-administered with a β2-agonist such as Bambuterol, U.S. Pat. No. 4,419,364 issued to Draco on Dec. 6, 1983; Bitolterol mesylate, U.S. Pat. No. 4,138,581 issued to Sterling Feb. 6, 1979; Carbuterol, U.S. Pat. No. 3,763,232 issued to Smith Kline Oct. 2, 1973; Clenbuterol, U.S. Pat. No. 3,536,712 issued to Boehringer Ingelheim Oct. 27, 1970; Dopexamine, U.S. Pat. No. 4,645,768 issued to Fisons Feb. 24, 1987; Formoterol, U.S. Pat. No. 3,994,974 issued to Yamanouchi Nov. 30, 1976; Mabuterol, U.S. Pat. No. 4,119,710 issued to Boehringer Ingelheim Oct. 10, 1978; Pirbuterol hydrochloride U.S. Pat. No. 3,700,681 issued to Pfizer Oct. 24, 1972; Procaterol hydrochloride U.S. Pat. No. 4,026,897 issued to Otsuka May 31, 1977; Ritodrine hydrochloride U.S. Pat. No. 3,410,944 issued to North American Philips Nov. 12, 1968; Brosaterol, U.S. Pat. No. 4,276,299 issued to Zambon Jun. 30, 1981 and U.S. Pat. No. 4,520,200 issued to Zambon May 28, 1985; Cimaterol, U.S. 4,407,819 issued to American Cyanamid Oct. 4, 1983; Docarpamine, U.S. 4,228,183 issued to Tanabe Oct. 14, 1980; Salmeterol, U.S. Pat. No. 4,992,474 issued to Glaxo Feb. 21, 1991 and U.S. Pat. No. 5,091,422 issued to Glaxo Feb. 25, 1992.

The compounds of formula I are particularly useful in the treatment of diseases or conditions that are advantageously treated by contomitant antagonism of both NK1 and NK3 receptors or NK1, NK2 and NK3 receptors. these diseases include neuropathy, such as diabetic or peripheral neuropathy and chemotherapy-induced neuropathy; asthma; osteoarthritis; rheumatoid arthritis; and migraine.

In a second alternative embodiment the compounds of formula I may be co-administered with another NK1 or NK2 antagonist such as those described in Appln No. DO-139125, filed 08-Jun-78, Pub. 12-Dec-79; Appln No. EP-82568, filed 22-Dec-81, Pub. 29-Jun-83; Appln No. EP-490379, filed 13-Dec-90, Pub. 17-Jun-92; Appln No. EP-353732, filed 05-Aug-88, Pub. 07-Feb-90; Appln No. EP-161007, filed 13-Jan-84, Pub. 13-Nov-85; Appln No. EP-385-43, filed 28-Feb-89, Pub. 05-Sep-90; Appln No. WO8301251, filed 09-Oct-81, Pub. 14-Apr-83; Appln No. BE-894602, filed 09-Oct-81, Pub. 31-Jan-83; Appln No. DE3205991, filed 19-Feb-82, Pub. 01-Sep-83; Appln No. EP-327009, filed 02-Feb-88, Pub. 09-Aug-89; Appln No. EP-336230, filed 05-Apr-88, Pub. 11-Oct-89; Appln No. 394989, filed 28-Apr-89, Pub. 31-Oct-90; Appln No. AU9068010, filed 22-Dec-89, Pub. 27-Jun-91; Appln No. EP-482539, filed 24-Oct-90, Pub. 29-Apr-92; Appln No. EP-443132, filed 10-Dec-90, Pub. 28-Aug-91; Appln No. EP-498069, filed 21-Dec-90, Pub. 12-Aug-92; Appln No. WO9222569, filed 19-Jun-91, Pub. 23-Dec-92; Appln No. JO4297492, filed 24-Oct-91, Pub. 21-Oct-92; Appln No. U.S. Pat. No. 4,997,853, filed 02-Dec-88, Pub. 05-Mar-91; Appln No. EP-272929, filed 24-Dec-86, Pub. 29-Jun-88; Appln No. EP-360390, filed 25-Jul-88, Pub. 28-Mar-90; Appln No. U.S. Pat. No. 3,862,114, filed 22-Nov-71, Pub. 21-Jan-75; Appln No. EP-219258, filed 30-Sep-85, Pub. 22-Apr-87, Appln No. U.S. Pat. No. 4,742,156, filed 30-Sep-85, Pub. 03-May-88; Appln No. EP-401177, filed 29-May-89, Pub. 05-Dec-90; Appln No. WO9202546, filed 03-Aug-90, Pub. 20-Feb-92; Appln No. EP-176436, filed 26-Sep-84, Pub. 02-Apr-86; Appln No. U.S. Pat. No. 4,680,283, filed 26-Sep-84, Pub. 14-Jul-87; Appln No. WO9220661, filed 22-May-91, Pub. 26-Nov-92; Appln No. EP-520555, filed 24-Jun-91, Pub. 30-Dec-92; Appln No. EP-347802, filed 20-Jun-88, Pub. 27-Dec-89; Appln No. EP-412542, filed 10-Aug-89, Pub. 13-Feb-91; Appln No. WO9005729, filed 23-Nov-88, Pub. 31-May-90; Appln No. WO9005525, filed 23-Nov-88, Pub. 31-May-90; Appln No. EP-436334, filed 04-Jan-90, Pub. 10-Jul-91; Appln No. WO9118878, filed 31-May-90, Pub. 12-Dec-91; Appln No. WO9118899, filed 01-Jun-90, Pub. 12-Dec-91; Appln No. WO9201688, filed 23-Jul-90, Pub. 06-Feb-92; Appln No. WO9206079, filed 28-Sep-90, Pub. 16-Apr-92; Appln No. WO9212152, filed 03-Jan-91, Pub. 23-Jul-92; Appln No. WO9212151, filed 10-Jan-91, Pub. 23-Jul-92; WO9215585, filed 01-Mar-91, Pub. 29-Apr-92; Appln No. WO022-676, filed 22-May-91, Pub. 26-Nov-92; Appln No. WO9221677, filed 31-May-91, Pub. 10-Dec-92; Appln No. WO9300331, filed 20-Jun-91, Pub. 07-Jun-93; Appln No. WO9300330, filed 21-Jun-91, Pub. 07-Jan-93; Appln No. WO9109844, filed 11-Jul-91, Pub. 11-Jul-91; Appln No. EP-429366, filed 23-Nov-89, Pub. 29-May-91; Appln No. EP-43077 1, filed 23-Nov-89, Pub. 05-Jun-91; Appln No. EP-514274, filed 17-May-91, Pub. 19-Nov-92; Appln No. EP-514276, filed 17-May-91, Pub. 19-Nov-92; Appln No. EP-514275, filed 17-May-91, Pub. 19-Nov-92; Appln No. EP-514273, filed 17-May-91, Pub. 19-Nov-92; Appln No. EP-428434, filed 06-Nov-89, Pub. 22-May-91; Appln No. EP-474561, filed 09-May-90, Pub. 11-Mar-92; Appln No. EP-512901, filed 03-May-91, Pub. 11-Nov-92; Appln No. EP-512902, filed 03-May-91, Pub. 11-Nov-92; Appln No. EP-515240, filed 03-May-91, Pub. 25-Nov-92; Appln No. US4472305, filed 17-May-83, Pub. 18-Sep-84; Appln No. US4839465, filed 20-Jan-87, Pub. 13-Jun-89; Appln No. EP-101929, filed 28-Jul-82, Pub. 07-Mar-84; Appln No. WO9102745, filed 16-Aug-89, Pub. 07-Mar-91; Appln No. U.S. Pat. No. 3,912,711, filed 03-Jul-72, Pub. 14-Oct-75; Appln No. U.S. Pat. No. 4,059,693, filed 11-Jun-76, Pub. 22-Nov-77; Appln No. U.S. Pat. No. 4,481,139, filed 13-Apr-83, Pub. 06-Nov-84; Appln No. U.S. Pat. No. 7,358,073, filed 24-Oct-88, Pub. 19-Dec-89; Appln No. U.S. Pat. No. 7,261,627, filed 24-Oct-88, Pub. 07-Mar-89, which are hereby incorporated by reference.

As may be appreciated by those of skill in the neurokinin art, that it is generally important to treat a patient with a neurokinin mediated disease, with an antagonist that is specific for the neurokinin receptors(s) mediating the disease. Thus a patient suffering from any of the diseases mediated by neurokinin-1 receptors, is generally most advantageously treated with a compound that is a potent antagonist of neurokinin-1, but is at most a weak antagonist of neurokinin-3. Even where antagonism of both neurokinin-1 and neurokinin-2 is desired, it is generally advantageous to avoid significant antagonism of neurokinin-3. Similarly, a patient suffering from any of the diseases mediated by neurokinin-3, is generally most advantageously treated with a compound that is a potent antagonist of neurokinin-3, but is at most a weak antagonist of neurokinin-1.

Accordingly, in a third embodiment the compounds of formula I are useful as a diagnostic tool for assessing the degree to which neurokinin-3 receptor activity (normal, overactivity or underactivity) is implicated in a patient's symptoms. In this regard a compound of formula I is used as an antagonist of the activity, for example including but not restricted to tachykinin agonist-induced inositol phosphate turnover or electrophysiological activation, of a cell sample obtained from a patient. Comparison of such activity in the presence or absence of a compound of formula I will disclose the degree of NK-3 receptor involvement in the mediation of agonist effects in that tissue.

Similarly, in a fourth embodiment, the compounds of formula I are useful in assessing the degree to which a selected pharmacological effect, as measured either in vitro or in vivo, is due to activation of the NK-3 receptor. In this instance the assays are performed in the presence or absence of a compound of formula I, and comparison of the results will disclose the degree of NK-3 receptor involvement.

The compounds of formula I are useful in the prevention and treatment of a wide variety of clinical conditions (as detailed in this specification) which are characterized by overstimulation of the tachykinin receptors, in particular NK1, NK2 and NK3.

These conditions may include disorders of the central nervous system such as anxiety, depression, psychosis and schizophrenia; neurodegenerative disorders such as AIDS related dementia, senile dementia of the Alzheimer type, Alzheimer's disease and Down's syndrome; demyelinating diseases such as multiple sclerosis and amyotrophic lateral sclerosis and other neuropathological disorders such as diabetic or peripheral neuropathy, AIDS related neuropathy, chemotherapy-induced neuropathy, and neuralgia; respiratory diseases such as chronic obstructive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatitis; addiction disorders such as alcholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function; fibrosing and collagen diseases such as scleroderma and eosinophilic fascioliasis; disorders of blood flow caused by vasodilation and vasospastic diseases such as angina, migraine and Reynaud's disease; and pain or nociception, for example, that is attributable to or associated with any of the foregoing conditions especially the transmission of pain in migraine. Hence, these compounds are readily adapted to therapeutic use for the treatment of physiological disorders associated with the overstimulation of the tachykinin receptors, in particular NK1, NK2 and NK3.

The compounds of the present invention are particularly useful in the treatment of pain or nociception and/or intimation and disorders associated therewith such as, for example: neuropathy, such as diabetic or peripheral neuropathy and chemotherapy-induced neuropathy; asthma; osteoarthritis; rheumatoid arthritis; and migraine.

For the treatment of any of these diseases compounds of Formula I may be administered orally, topically, parenterally, ICV, by inhalation spray or rectally in dosage unit formulations containing conventional non-toxic pharmaceutically acceptable carders, adjuvants and vehicles. The term parenteral as used herein includes subcutaneous injections, intravenous, intramuscular, intracistemal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl- pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula I are employed. (For purposes of this application, topical application shall include mouth washes and gargles.)

In the treatment of a condition associated with an excess of tachykinins, an appropriate dosage level will generally be about 0.001 to 50 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.00 1 to 25 mg/kg per day, about 0.005 to 10 mg/kg per day, or about 0.005 to 5 mg/kg per day. Within this range the dosage may be 0.005 to 0.05, 0.05 to 0.5 or 0.5 to 5.0 mg/kg per day. The compounds may be administered on a regimen of 1 to 4 times per day, preferably once or twice per day.

TACHYKININ ANTAGONISM ASSAY

The compounds of this invention are useful for antagonizing tachykinins, in particular substance P and neurokinin A in the treatment of gastrointestinal disorders, central nervous system disorders, inflammatory diseases, pain or migraine and asthma in a mammal in need of such treatment. This activity can be demonstrated by the following assay.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 μg of the plasmid DNA into 10 million COS cells was achieved by electroporation in 800 μl of transfection buffer (135 mM NaCl, 1.2 mM CaCl$_2$, 1.2 mM MgCl$_2$, 2.4 mM K$_2$HPO$_4$, 0.6 mM KH$_2$PO$_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100U/ml penicillin-streptomycin, and 90% DMEM media (GIBCO, Grand Island, N.Y.) in 5% CO$_2$ at 37° C. for three days before the binding assay.

Similar methods were used to express the human NK2 and NK3 receptors.

B. Stable Expression in CHO

To establish a stable cell line expressing the cloned human NK1R, the cDNA was subcloned into the vector pRcCMV (INVITROGEN). Transfection of 20 μg of the plasmid DNA into CHO cells was achieved by electroporation in 800 μl of transfection buffer suplemented with 0.625 mg/ml Herring sperm DNA at 300 V and 950 uF using the IBI GENEZAPPER (IBI). The transfected cells were incubated in CHO media [10% fetal calf serum, 100 U/ml pennicilin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)] in 5% CO$_2$ at 37° C. until colonies were visible. Each colony was separated and propagated. The cell clone with the highest number of human NK1R was selected for subsequent applications such as drug screening.

Similar methods were used to express the human NK2 and NK3 receptors.

C. Assay Protocol using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM MnCl$_2$, 150 mM NACl, 0.04 mg/ml bacitracin, 0.004 mg/ml leupeptin, 0.02 mg/ml BSA, 0.01 mM phosphoramidon) such that 200 μl of the cell suspension would give rise to about 10,000 cpm of specific $^{125}$I-SP binding (approximately 50,000 to 200,000 cells). In the binding assay, 500 ul of cells were added to a tube containing 20 μl of 1.5 to 0.25 nM of $^{125}$I-SP and 5 μl of unlabeled substance p or any other test compound in DMSO. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM MnCl$_2$, 150 mM NaCl) three times and its radioactivity was determined by gamma counter. A similar assay was used for NK2 and NK3 except $^{125}$I-NKA or $^{125}$I-methyl-Phe$^7$-NKB were used as the ligand.

The activation of phospholipase C by NK1R may also be measured in CHO cells expressing the human NK1R by determining the accumulation of inositol monophosphate which is a degradation product of IP$_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1N HCl is added. Each well is sonicated at 4° C. and extracted with CHCl$_3$/methanol (1:1). The aqueous phase is applied to a 1 ml Dowex AG 1×8 ion exchange column. The column is washed with 0.1N formic acid followed by 0.025M ammonium formate-0.1N formic acid. The inositol monophosphate is eluted with 0.2M ammonium formate-0.1N formic acid and quantitated by beta counter. similar methods were used to assess antagonism at the NK2 and NK3 receptors, except NKA or NKB were used as the stimulating agonists.

The compounds of of Formula I as Exemplified in the EXAMPLES below have been found to displace radioactive ligand for the NK-1 receptor at a concentration range of 0.01 nM to 1.0 μM, for the NK-2 receptor, 0.01 nM to 5 μM, and for the NK-3 receptor, 1.0 nM to 10 μM. Further data is provided in Table 1.

TABLE I

[Structure: piperazine-N-CH2CH2CH2-CH(Ar)-C(O)-N(CH3)-CH2-Ph, where Ar = 3,4-dichlorophenyl, and piperazine has substituent X]

IC50

| X-N group | NK1(nM) | NK2(nM) | NK3(nM) |
|---|---|---|---|
| H3C-C(O)-NH-C(Ph)(piperidine)- | 250 | 45 | 1.5 |
| Ph-C(piperidine)- (4-phenylpiperidine) | 100 | 200 | 8 |
| indane-spiro-piperidine | 500 | 200 | 8 |
| CH3C(O)-N(CH2-)-(2-substituted phenyl)-spiro-piperidine | — | 30 | 0.75 |
| MeSO2-N(CH2-)-(2-substituted phenyl)-spiro-piperidine | — | 30 | 0.6 |
| Ph-N(piperazine)- | 250 | — | 3 |
| 2-pyridyl-piperazine | 220 | — | 4 |

TABLE I-continued

[Same core structure]

IC50

| X-N group | NK1(nM) | NK2(nM) | NK3(nM) |
|---|---|---|---|
| 1-oxo-indane-spiro-piperidine | — | 40 | 1 |

Several methods for preparing the compounds of this invention are illustrated in the following Schemes and Examples.

The compounds of the present invention are prepared by alkylating azacycle 1, in which $R_1$=H, under appropriate conditions (Scheme 1). The required azacycle staging materials are prepared using methods described in the literature; more specifically, as described in Ong, H. H. et al, Journal of Medicinal Chemistry, 1983,26, 981-986, and Nargund, R. et al, Merck patent application no. 18899. None of the compounds in these references are claimed to be neurokinin antagonists.

Thus, azacycle 1 ($R_1$=H) is combined with the appropriate aldehyde and the intermediate imine is reduced to the tertiary amine chemically (e.g. using sodium cyanoborohydride) or catalytically (e.g. using hydrogen and palladium on carbon or Raney nickel catalyst) (Scheme 1). The aldehyde needed for this reaction can be prepared by methods generally known in the chemical literature; for the purposes of the present invention the preparation of a representative aldehyde is described in Hale, J. J.; Finke, P. E.; MacGoss, M. *Bioorganic and Medicinal Chemistry Letters*, 2, (Feb. 1993).

In an alternative embodiment of the present invention, azacycle 1 ($R_1$=H) can be alkylated with an alkyl halide or alkyl sulfonate ester (with or without an added base to neutralize the mineral acid or sulfonic acid by-product) to give the desired compound (Scheme 1). The alkyl halide or alkyl sulfonate needed for this reaction can be prepared by methods generally known in the chemical literature; for the purposes of the present invention an aldehyde, prepared as described above, can be reduced to an alcohol with sodium borohydride, diisobutylaluminum hydride or lithium aluminum hydride, and the product alcohol convened to either the alkyl halide using methods described in March J. "Advanced Organic Chemistry", 3rd ed., John Wiley & Sons, New York, pp. 382-384 (1985), or alkyl sulfonate ester using methods described in March J. "Advanced Organic Chemistry", 3rd ed., John Wiley & Sons, New York, p. 444 (1985).

In an alternative embodiment of the present invention, 1 ($R_1$=H) can be acylated to give the tertiary amide and subsequent reduction with a strong reducing agent (e.g. diborane including borane dimethylsulfide; and, lithium aluminum hydride) will give the desired compound (Scheme 1). The acylating agent needed for this reaction can be prepared by methods generally known in the chemical literature; for the purposes of the present invention an aldehyde, prepared as described above, can be oxidized using such commonly used reagents as permanganate in acid or silver oxide, and the resulting acid activated as an acid chloride or mixed anhydride which can be used to acylate 1 ($R_1$=H). The product amide can in and of itself be a neurokinin antagonist or can be reduced with a strong reducing agent, such as diborane of lithium aluminum hydride, to give the tertiary amine.

Optionally, compound 1 formed in the alkylation step may be further modified in subsequent reactions. In one illustration of such an approach, the aldehyde fragment contained a t-butoxycarbonylamino group (Example 2). After reductive amination, the t-butoxycarbonyl protecting group is removed by treatment with a strong acid such as trifluoroacetic acid or formic acid and the resulting amine is acylated to furnish the desired compounds (Example 3). Alternatively, the protecting group may also be present in the azacycle portion as illustrated with a benzyloxycarbonyl group in Example 6. Thus an azacycle containing a benzyloxycarbonylindoline (prepared in example 4) is alkylated with an aldehyde in the presence of a reducing agent. Next, the protecting group is removed to liberate a free amine (example 7) and the amine is further reacted to provide additional analogs (Example 8).

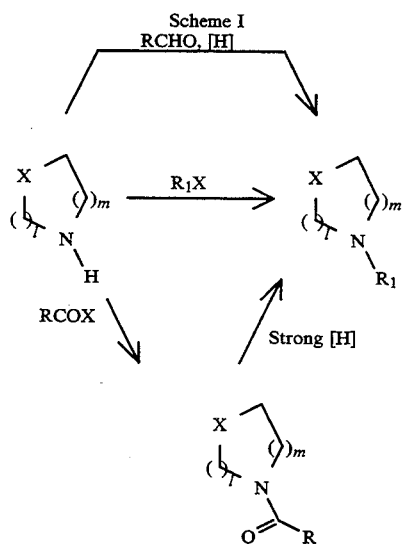

Scheme I

EXAMPLE 1

3-(S)-(3,4-Dichlorophenyl)-4-(N-benzyl-N-methylamino)-4-oxo-butanal.

A solution of 4.8 g (19.6 mmol) of 2-(S)-(3,4-dichlorophenyl)-4-pentenoic acid in 50 mL of $CH_2Cl_2$ and 10 drops of DMF was cooled in an ice bath and 1.8 mL of oxalyl chloride was added. The solution was stirred for 15 min after gas evolution had ceased. The mixture was concentrated in vacuo and the residue was diluted with 50 mL of $CH_2Cl_2$. The solution was cooled in ice bath as 2.6 mL (20.4 mmol) of N-benzyl-methyl amine and 1.7 mL (21 mmol) of pyridine were added. After stirring for 1 h at ice bath temperature the solution was diluted with $CH_2Cl_2$ and washed with water, 1.2N HCl and brine. The solution was dried over $Na_2SO_4$ and concentrated to give N-benzyl-N-methyl-2(S)-(3,4-dichlorophenyl)-4-pentenoamide as an oil.

$^1$H NMR (CDCl$_3$, ppm ranges are given because of amide rotomers and line broadening) δ 2.4 (m, 1H); 2.8 (m, 1H); 2.82 and 2.95 (2 s, 3H); 3.52–3.8 (m, 1H); 4.32 and 4.6 (ABq) and 4.57 (s, 2H); 5.0(m, 2H), 5.7 (m, 1H), 6.9–7.4 (m, 8H).

The amide obtained above was dissolved in 40 mL of acetone, 20 mL of t-butanol and 20 mL of water. To this solution 5 mg of Osmium tetroxide and 2.5 g (21.4 mmol) of 4-methylmorpholine N-oxide were added. After stirring overnight, the reaction was quenched with approximately 2 g of $Na_2SO_3$ and concentrated to 25% of the original volume. The residue was partitioned between water and 1:1 ether ($Et_2O$), ethyl acetate (EtOAc), the layers were separated and the aqueous layer was extracted with $Et_2O$:EtOAc. Each organic layer was washed with water, brine and dried by filtering through $Na_2SO_4$. The filtrate was concentrated to afford the crude diol.

A solution of the diol in 60 mL of tetrahydrofuran (THF) and 20 mL of water was treated with 4.5 g (21 mmol) of Sodium periodate. After stirring for 2 h, the reaction was diluted with $Et_2O$:EtOAC and washed with water and brine. The organic layer was dried ($Na_2SO_4$) and the filtrate was concentrated. The residue was purified by flash column chromatography using a gradient of 30–50% EtOAC/hexane to furnish 3.7 g (54% yield for three steps) of the title compound as a thick oil.

$^1$H NMR (CDCl$_3$, ppm ranges are given because of amide rotomers and line broadening) δ 2.65 (m, 1H); 2.85 and 2.91 (2 s, 3H); 3.54 (m, 1H); 4.25–4.65 (m, 3H), 7.0–7.4 (m, 8H); 9.75 and 9.78 (2 s, 1H).

Mass Spectrum (CI) 351 ($^{37}$Cl+$^{35}$Cl isotope), 349 ($^{35}$Cl+$^{35}$Cl isotope).

EXAMPLE 2

1'[3-(S)-(3,4-dichlorophenyl)-4-(N-benzyl-N-methyl-)amino-4-oxo-butyl]-1-methanesulfonyl-spiro[indoline-3,4'-piperidine].

To a solution of 0.36 g (1.03 mmol) of 3-(S)-(3,4-dichlorophenyl)-4-(N-benzyl-N-methyl)amino-4-oxo-butanal (Example 1) in 3 mL of methanol were added 0.32 g (1.05 mmol) of 1-methanesoufonyl-spiroindoline-3,4'-piperidine hydrochloride and 0.3 g of powedered 4 Å molecular sieves. After 1 h, 1N NaCNBH$_3$ in THF (3 mL) was added over 10 min with a syringe pump. Afeter 1 h, when the reaction was complete by TLC, the mixture was filtered through a pad of celite, the reaction flask and the pad were rinsed with methanol. The filtrate was concentrated to approximately 5 ml and the residue was partitioned between saturated NaHCO$_3$ and $Et_2O$:EtOAC. The organic layer was washed with water, brine and dried over NA$_2$SO$_4$. The filtrate was concentrated and the residue was chromatographed on a flash column using 49:49:2 EtOAc: Hexane: triethylamine to furnish 0.52 g (84%) of the title compound as a foam.

$^1$H NMR (CDCl$_3$, ppm ranges are given because of amide rotomers and line broadening) δ 1.5–2.9 (m, 12 H), 2.87 & 2.88 (2 s, 3 H), 2.88 & 2.98 (2 s, 3 H), 3.73 &

3.76 (2 s, 2H), 3.9 (m, 1H), 4.3–4.7 (m, 2H), 7.0–7.5 (m, 12 H).

Mass Spectrum (CI) 602 ($^{37}$Cl+$^{35}$Cl isotope), 600 ($^{35}$Cl+$^{35}$Cl isotope).

The following compounds were prepared by reacting the appropriate amine with 3-(S)-(3,4-dichlorophenyl)-4-(N-benzyl-N-methyl)amino-4-oxo-butanal (Example 1) according to the procedure of Example 2.

EXAMPLE 3

1'[3-(S )-(3,4-dichlorophenyl )-4-(N-benzyl-N-methyl)amino-4-oxo-butyl]-spiro[1H-indene-1,4'-piperidine].

$^1$H NMR (CDCl$_3$, ppm ranges are given because of amide rotomers and line broadening) δ 1.2–3.0 (m, 12 H), 2.91 & 2.99 (2 s, 3 H), 3.9 (m, 1H), 4.4–4.7 (m, 2 H), 6.7 (m, 2H), 7.0–7.5 (m, 12 H).

Mass Spectrum (CI) 521 ($^{37}$Cl+$^{35}$Cl isotope), 519 ($^{35}$Cl+$^{35}$Cl isotope).

EXAMPLE 4

1'[3-(S )-(3,4-dichlorophenyl)-4-(N-benzyl-N-methyl)amino-4-oxo-butyl]-spiro[(3-indanone)-1,4'-piperidine].

$^1$H NMR (CDCl$_3$, ppm ranges are given because of amide rotomers and line broadening) δ 1.4–3 (m, 12 H), 2.51 & 2.54 (2 s, 2 H), 2.89 & 2.98 (2 s, 3 H), 3.9 (m, 1H), 4.3–4.7 (m, 2H), 7.05–7.75 (m, 12 H).

Mass Spectrum (CI) 537 ($^{37}$Cl+$^{35}$Cl isotope), 535 ($^{35}$Cl+$^{35}$Cl isotope).

EXAMPLE 5

1-[3-(S)-(3,4-dichlorophenyl)-4-(N-benzyl-N-methyl)amino-4-oxo-butyl]-4-phenyl-4-acetamido-piperidine.

$^1$H NMR (CDCl$_3$, ppm ranges are given because of amide rotomers and line broadening) δ 1.5–2.8 (m, 12 H), 1.97 & 1.98 (2 s, 3 H), 2.87 & 2.97 (2 s, 3 H), 3.9 (m, 1 H), 4.3–4.7 (m, 2 H), 5.5 (br d, 1 H), 7.0–7.45 (m, 13 H).

Mass Spectrum (CI) 554 ($^{37}$Cl+$^{35}$Cl isotope), 552 ($^{35}$Cl+$^{35}$Cl isotope).

EXAMPLE 6

1-[3-(S)-(3,4-dichlorophenyl)-4-(N-benzyl-N-methyl)amino-4-oxo-butyl]-4-benzyl-piperazine.

To a solution of 0.12 g (0.34 mmol) of 3-(S)-(3,4-Dichlorophenyl)-4-(N-benzyl-N-methyl)amino-4-oxo-butanal (Example 1) in 2 mL of methanol were added 57 μL (0.33 mmol) of N-benzyl-piperazine, 18 μL (0.31 mmol) of acetic acid and 0.2 g of powedered 4 Å molecular sieves. After 1 h, 1N NaCNBH3 in THF (0.8 mL) was added over 10 min with a syringe pump. After 1 h, when the reaction was complete by TLC, the mixture was filtered through a pad of celite, the reaction flask and the pad were rinsed with methanol. The filtrate was partitioned between saturated NaHCO3 and Et-2O:EtOAC. The organic layer was washed with water, brine and dried over NA$_2$SO$_4$. The filtrate was concentrated and the residue was purified by prep TLC using 2% Et3N/EtOAc to furnish 97 mg (58%) of the title compound as a foam.

$^1$H NMR (CDCl$_3$, ppm ranges are given because of amide rotomers and line broadening) δ 1.5–2.8 (m, 12 H), 2.86 & 2.95 (2 s, 3 H), 3.46 & 3.48 (2 s, 2 H), 3.9 (m, 1 H), 4.3–4.7 (m, 2 H), 7.0–7.5 (m, 13 H).

Mass Spectrum (CI) 512 ($^{37}$Cl+$^{35}$Cl isotope), 510 ($^{35}$Cl+$^{35}$Cl isotope).

The following compounds were synthesized by substituting the required amine for N-benzyl-piperazine in example 6.

EXAMPLE 7

1-[3-(S)-(3,4-dichlorophenyl)-4-(N-benzyl-N-methyl)amino-4-oxo-butyl]-4-phenyl-piperidine].

$^1$H NMR (CDCl$_3$, ppm ranges are given because of amide rotomers and line broadening) δ 1.5–3.0 (m, 12 H), 2.89 & 2.97 (2 s, 3 H), 3.4–4.1 (m, 1 H), 3.95 (m, 1 H), 4.3–4.7 (m, 2 H), 7.0–7.5 (m, 13 H).

Mass Spectrum (CI) 497 ($^{37}$Cl+$^{35}$Cl isotope), 495 ($^{35}$Cl+$^{35}$Cl isotope).

EXAMPLE 8

1 -[3-(S)-(3,4-dichlorophenyl)-4-(N-benzyl-N-methyl)amino-4-oxo-butyl]-4-(2-pyridyl)-piperazine.

$^1$H NMR (CDCl$_3$, ppm ranges are given because of amide rotomers and line broadening) δ 1.6 (br, 1 H), 1.85 (m, 1 H), 2.2–2.6 (m, 6 H), 2.87 & 2.97 (2 s, 3 H), 3.46 (m, 4 H), 3.9 & 4.0 (2 t, 1 H, J=7 Hz), 4.3–4.7 (m, 2 H) 6.61 (m, 2 H), 7.0–7.5 (m, 9 H), 8.16 (m, 1 H).

Mass Spectrum (CI) 499 (37Cl+$^{35}$Cl isotope), 497 ($^{35}$Cl+$^{35}$Cl isotope).

EXAMPLE 9

1'[3-(S)-(3,4-dichlorophenyl)-4-(N-benzyl-N-methyl)amino-4-oxo-butyl]-1-acetyl-spiro[indoline-3,4'-piperidine].

$^1$H NMR (CDCl$_3$, ppm ranges are given because of amide rotomers and line broadening) δ 1.5–3.0 (m, 12 H), 2.22 & 2.23 (2 s, 3 H), 2.89 & 2.98 (2 s, 3 H), 3.78 & 3.81 (2 s, 2 H), 3.9 (m, 1 H), 4.3–4.7 (m, 2 H), 7.0–7.5 (m, 11 H), 8.18 (d, 1 H, J=8 Hz).

Mass Spectrum (CI) 566 (37Cl+$^{35}$Cl isotope), 564 ($^{35}$Cl+$^{35}$Cl isotope).

---

What is claimed is:
1. A compound of Formula Ia

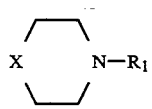

wherein the group

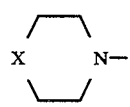

is selected from the group consisting of

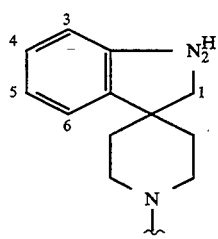

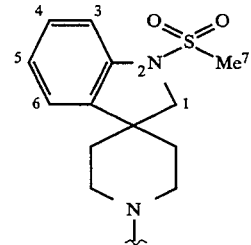

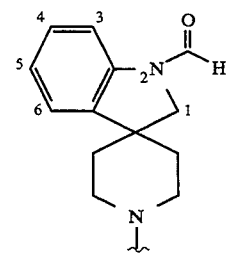

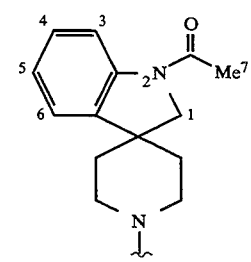

R₁ is

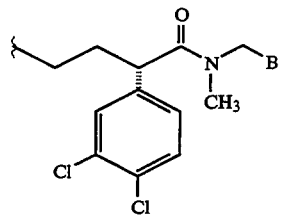

where B is selected from:
(a) phenyl or mono- or di-substituted phenyl wherein the substituents are independently chloro, methyl, phenyl or CF₃;
(b) pyridyl or mono-, di- or tri-substituted pyridyl wherein the substituents are independently chloro, methyl, phenyl or CF₃; and
(c) thiophene or mono- or di-substituted thiophene wherein the substitutents are independently chloro, methyl, phenyl or CF₃.

2. A compound selected from the group consisting of:
(a) 1'[3-(S)-(3,4-dichlorophenyl)-4-(N-benzyl-N-methyl)amino-4-oxo-butyl]-1-methanesulfonyl-spiro[indoline-3,4'-piperidine];
(b) 1'[3-(S)-(3,4-dichlorophenyl)-4-(N-benzyl-N-methyl)amino-4-oxo-butyl]-spiro[1H-indene-1,4'-piperidine];
(c) 1'[3-(S)-(3,4-dichlorophenyl)-4-(N-benzyl-N-methyl)amino-4-oxo-butyl]-spiro[(3-indanone)-1,4'-piperidine];
(d) 1'[3-(S)-(3,4-dichlorophenyl)-4-(N-benzyl-N-methyl)amino-4-oxo-butyl]-1-acetyl-spiro[indoline-3,4'-piperidine].

3. A compound according to claim 1 wherein B is phenyl or mono or di- substituted phenyl wherein the substitutents are independently chloro, methyl, phenyl or CF₃.

4. A method of treating or preventing asthma in a pateint in need thereof which comprises the administration to the patient of a non-toxic therapeutically effective amount of the compound of claim 1.

* * * * *

--- the substituents residing at 1 or 3 of the positions 1,3,4,5,or 6 of the above groups the substituents selected from the group consisting of:
(1) hydroxy,
(2) oxo,
(3) cyano,
(4) —NHR₆,
(5) —NR₆R₇,
(6) —NR₆COR₇,
(7) —halogen,
(8) —CF₃,
(9) —C₁₋₃alkyl,
(10) —S(O)₂ C₁₋₃alkyl wherein R₆ and R₇ are hydrogen or C₁₋₃alkyl, or mono- or di-substituted C₁₋₃alkyl, the substituents independently selected from:
(1) C₁₋₃alkoxy,
(2) hydroxy,
(3) oxo,
(4) halogen; and